(12) United States Patent
Toyoda et al.

(10) Patent No.: US 6,580,600 B2
(45) Date of Patent: Jun. 17, 2003

(54) CAPACITANCE TYPE HUMIDITY SENSOR AND MANUFACTURING METHOD OF THE SAME

(75) Inventors: Inao Toyoda, Okazaki (JP); Hajime Matsuhashi, Nagoya (JP); Kazushi Asami, Okazaki (JP)

(73) Assignees: Nippon Soken, Inc., Nishio (JP); Denso Corporation, Kariya (JP)

( * ) Notice: Subject to any disclaimer, the term of this patent is extended or adjusted under 35 U.S.C. 154(b) by 0 days.

(21) Appl. No.: 10/157,197

(22) Filed: May 30, 2002

(65) Prior Publication Data

US 2002/0141136 A1 Oct. 3, 2002

Related U.S. Application Data (63) Continuation-in-part of application No. 10/054,978, filed on Jan. 25, 2002.

(30) Foreign Application Priority Data

Feb. 20, 2001 (JP) .......................................... 2001-43973
Jun. 7, 2001 (JP) ......................................... 2001-173034

(51) Int. Cl.[7] ................................................ H01G 9/00
(52) U.S. Cl. ....................... 361/523; 361/528; 361/503; 361/512; 361/510; 29/25.03
(58) Field of Search ................................ 361/523, 286, 361/301, 303, 284, 528, 502, 503, 508, 509, 512, 514; 29/25.03

(56) References Cited

U.S. PATENT DOCUMENTS

| | | | |
|---|---|---|---|
| 4,057,823 A | | 11/1977 | Burkhardt et al. |
| 4,144,636 A | | 3/1979 | Burkhardt et al. |
| 4,305,112 A | | 12/1981 | Heywang et al. |
| 4,564,882 A | * | 1/1986 | Baxter et al. |
| 4,651,121 A | * | 3/1987 | Furubayashi et al. |
| 4,698,657 A | * | 10/1987 | Watanabe et al. |
| 4,893,214 A | | 1/1990 | Nishiwaki et al. |
| 5,040,411 A | * | 8/1991 | Medzius |
| 5,050,434 A | * | 9/1991 | Demisch |
| 5,177,662 A | * | 1/1993 | Thoma |
| 5,254,371 A | * | 10/1993 | Hegner et al. |
| 5,396,795 A | | 3/1995 | Araki |
| 5,883,009 A | | 3/1999 | Villa et al. |
| 6,111,280 A | | 8/2000 | Gardner et al. |

FOREIGN PATENT DOCUMENTS

| | | |
|---|---|---|
| GB | 2149922 A | 6/1985 |
| JP | U-57-130257 | 8/1982 |
| JP | A-59-112256 | 6/1984 |
| JP | A-61-281958 | 12/1986 |
| JP | A-63-058249 | 3/1988 |
| JP | A-2-093357 | 4/1990 |
| JP | A-5-45320 | 2/1993 |
| JP | U-5-23124 | 3/1993 |
| JP | A-5-144877 | 6/1993 |
| JP | A-6-138074 | 5/1994 |
| JP | A-7-20080 | 1/1995 |
| JP | B2-3042992 | 3/2000 |

* cited by examiner

Primary Examiner—Dean A. Reichard
Assistant Examiner—Nguyen Ha
(74) Attorney, Agent, or Firm—Posz & Bethards, PLC (57) ABSTRACT

A capacitance type humidity detecting sensor has two electrodes opposing each other with a gap interposed therebetween to form a capacitor on a silicon substrate with a silicon oxide film formed on a surface thereof. A moisture-sensitive film is formed so as to cover the two electrodes with a silicon nitride film interposed therebetween. The silicon nitride film protects the two electrodes from moisture passing through the moisture-sensitive film. The capacitance formed between the two electrodes changes in accordance with ambient humidity. A switched capacitor circuit formed in a circuit element portion processes a signal indicative of a change in the capacitance formed between the two electrodes.

24 Claims, 7 Drawing Sheets

CAPACITANCE TYPE HUMIDITY SENSOR AND MANUFACTURING METHOD OF THE SAME

CROSS REFERENCE TO RELATED APPLICATION

This application is a CIP application of U.S. application Ser. No. 10/054,978 filed on Jan. 25, 2002. This application is based upon Japanese Patent Applications Nos. 2001-43973 filed on Feb. 20, 2001, and 2001-173034 filed on Jun. 7, 2001, the contents of which are incorporated herein by reference.

BACKGROUND OF THE INVENTION

1. Field of the Invention

The present invention relates to a capacitance type humidity sensor in which a moisture-sensitive film is disposed between two electrodes to increase permittivity of a capacitance between the two electrodes, and to a manufacturing method of the same.

2. Related Art

A humidity sensor such as the one disclosed in JP-A-60-166854 has a substrate as a lower electrode, a moisture-sensitive film formed on the substrate, and a thin upper electrode having moisture permeability. However, as the upper electrode is exposed to sensing conditions, it is required to have high resistivity against such conditions.

To the contrary, as is disclosed in JU-A-5-23124 or JPA-7-20080, a proposed sensor includes two opposing electrodes formed on an identical plane of a substrate, and a moisture-sensitive film is formed on these two electrodes. However, a resistance detection type sensor is mainly disclosed in these references while a capacitance detection type sensor is only briefly and generally described. Further, although these electrodes are disposed under the moisture-sensitive film, the electrodes are nonetheless exposed to water because moisture can reach the electrodes through the moisture-sensitive film. Therefore, a problem arises because the electrodes must be water resistant. Consequently, precious metal is preferably used to form the electrodes to ensure reliability of the electrodes against moisture. However, the precious metal increases manufacturing cost and becomes a contaminant in the manufacturing process.

Incidentally, the sensor disclosed in JU-A-5-23124 has a dielectric material as a base plate, and therefore a discrete circuit board is required. The sensor plate is electrically connected to the circuit plate by wiring that increases stray capacitance. Therefore, the capacitance in a detection portion should be designed so as to be large to increase the signal to noise ratio. As a result, the size of the sensor body inevitably increases.

SUMMARY OF THE INVENTION

An object of the invention is to provide a humidity sensor that has high reliability. Alternatively, another object of the invention is to provide a humidity sensor that can be produced in a semiconductor process line, and a manufacturing method of the same.

According to an aspect of the present invention, a first insulation film is formed on a semiconductor substrate. First and second electrodes are disposed on the first insulation film and oppose each other with a gap interposed therebetween. A second insulation film is formed so as to cover the first and second electrodes. Moreover, a moisture-sensitive film is formed so as to cover the second insulation film.

In this structure, the second insulation film is interposed between the first and second electrodes and the moisture-sensitive film, so that the electrodes are water resistant.

According to a second aspect of the present invention, a circuit portion is integrated in the semiconductor substrate in which a humidity sensing portion is formed. The circuit portion processes signals transmitted from the sensing portion.

Preferably, the first and second electrodes are composed of the same material as that of wiring in the circuit portion. Thus, the electrodes and the wiring are simultaneously formed.

Also, the circuit portion preferably includes a switched capacitor circuit that can detect small capacitance amounts.

In addition, the second insulation film is preferably composed of a silicon nitride film. The silicon nitride film has a relatively high dielectric constant, so that capacitance between the first and second electrodes increases.

Preferably, the first insulation film is composed of a material that has a dielectric constant lower than that of the second insulation film. Thus, parasitic capacitance between the electrodes and the substrate can be decreased.

Incidentally, a molecular organic material that has a high hygroscopicity, such as polyimide or butyric acetylcellulose, can be employed as the moisture-sensitive film.

Preferably, the respective electrodes have a comb-shaped pattern having electrode portions, and the electrode portions of the first electrode are interleaved with those of the second electrode to increase a facing area between the electrode portions of the first and second electrode.

Incidentally, the electrodes may be composed of a material such as Al, Al—Si, Ti, Au, Cu, and poly-Si, or a compound composed of at least two of those materials.

Preferably, the moisture-sensitive film is disposed so that a surface thereof contacting the second insulation film is located lower than top surfaces of the first and second electrodes, to thereby dispose the moisture-sensitive film in the gap formed between the electrodes.

Incidentally, the sensing portion is formed after the circuit portion is formed.

According to a third aspect of the present invention, a moisture-sensing base is mounted on a supporting substrate so that a signal having a change in capacitance that is detected in the moisture-sensing base is outputted through a wiring electrode portion formed in the supporting substrate. In this case, a moisture-sensitive film faces the supporting substrate, a connecting electrode portion for outputting a signal from the moisture-sensing base to the wiring electrode portion is disposed between the moisture-sensing base and the supporting substrate. The wiring electrode portion is protected from ambient conditions by a coating material.

Other features and advantages of the present invention will become more apparent from the following detailed description made with reference to the accompanying drawings.

DETAILED DESCRIPTION OF THE PREFERRED EMBODIMENT

Specific embodiments of the present invention will now be described hereinafter with reference to the accompanying drawings in which the same or similar component parts are designated by the same or similar reference numerals.

(First Embodiment)

Figure 1:
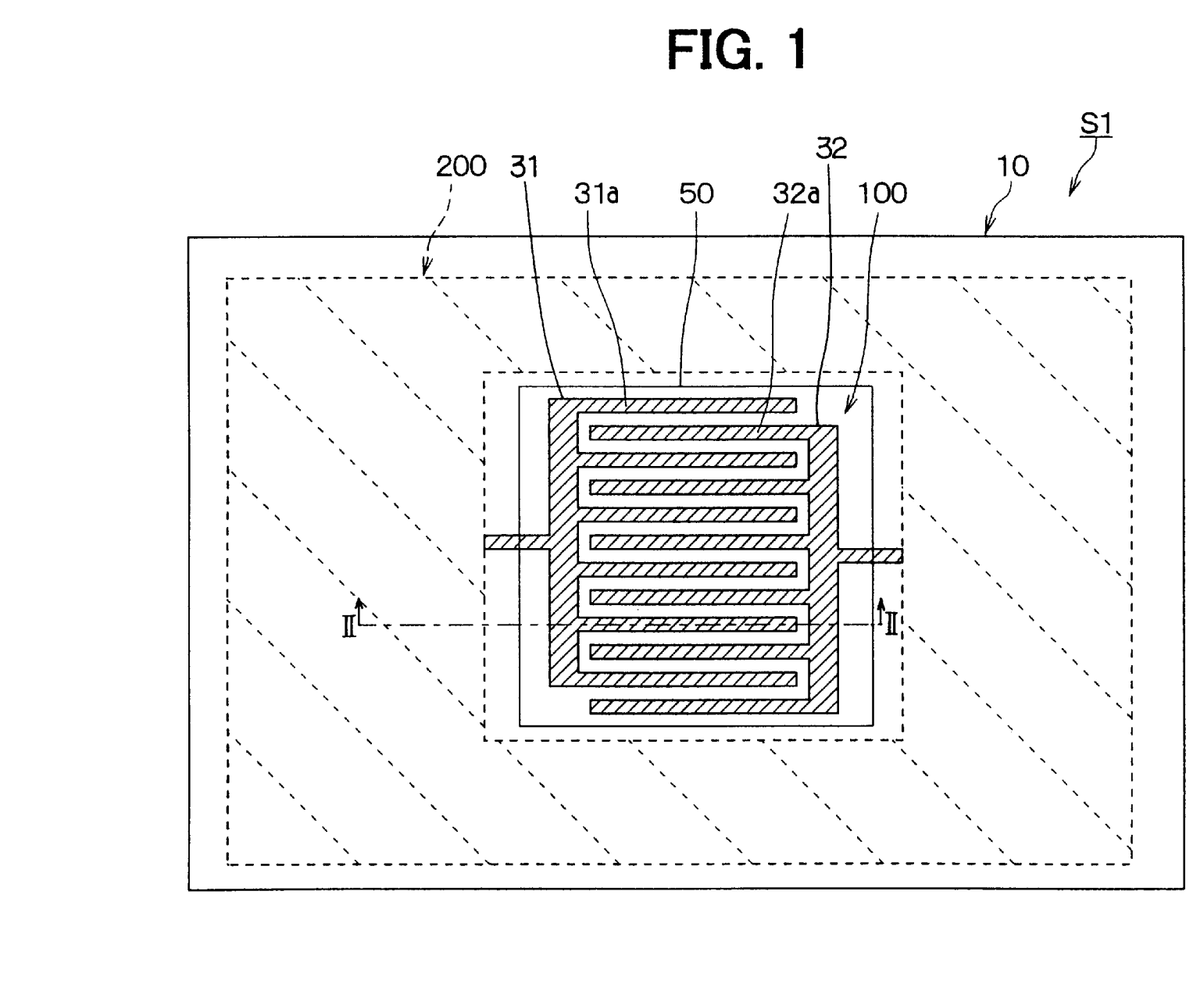
FIG. 1 is a schematic plan view of a capacitance type humidity sensor of a first embodiment of the present invention.

A humidity sensor (sensor chip) S1 shown in FIG. 1 may be used for humidity control in an air conditioner or to detect humidity for weather observation purposes.

An N-type silicon substrate is employed as a semiconductor substrate 10. A silicon oxide film 20 is formed on the semiconductor substrate 10 as a first insulation film. First and second electrodes 31, 32 (hereinafter, referred to as detection electrodes) are formed on an identical plane of the silicon oxide film 20 so as to oppose each other with a gap interposed therebetween.

Although the shape of the detection electrodes 31, 32 is not restricted, in this embodiment, the electrodes 31, 32 have a comb-shaped pattern constituted by plural electrode portions 31a, 32a, respectively. The plural electrode portions 31a, 32a of the both electrodes 31, 32 have a bar-like shape, respectively, and the plural electrode portions 31a of the detection electrode 31 alternate with those of the detection electrode 32 in an interlocking pattern, thereby decreasing an arrangement area for the detection electrodes 31, 32.

A material capable of being used in a normal semiconductor producing line can be used to form the detection electrodes 31, 32. The material is, for example, Al, Al—Si (which contains minute amounts of Si in such a degree at, for example, less than 1%), Ti, Au, Cu, poly-Si or the like. Incidentally, the electrodes 31, 32 are composed of Al in this embodiment.

Figure 2:
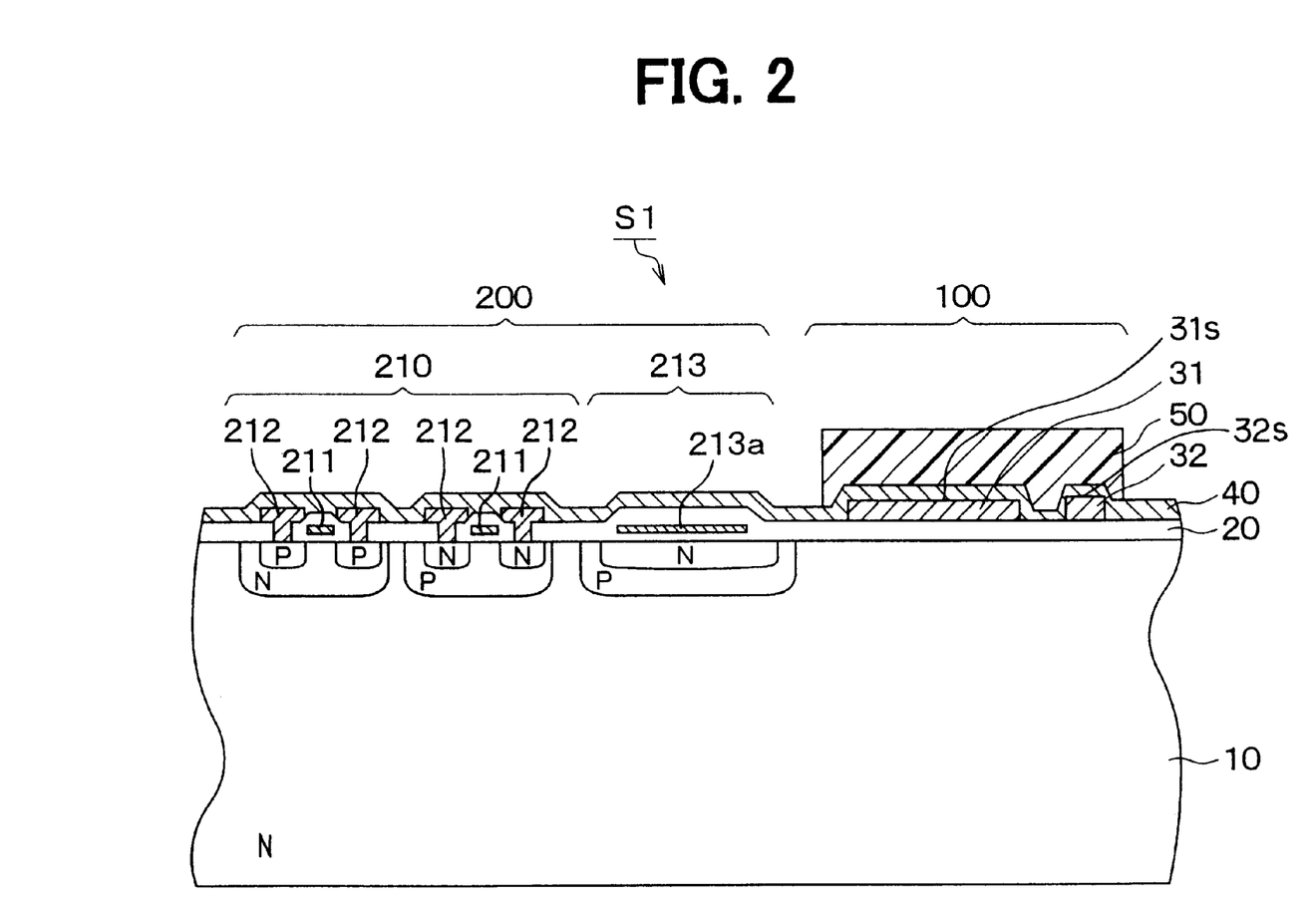
FIG. 2 is a schematic cross sectional view taken along line II—II in FIG. 1.

A silicon nitride film 40 is formed on the electrodes 31, 32 as a second insulation film. Although the silicon nitride film 40 is shown as covering gaps formed between the electrodes 31, 32 as well as the electrodes 31, 32, the silicon nitride film 40 may only cover the electrodes 31, 32 and may not cover the gaps.

A moisture-sensitive film 50 having a permittivity that changes according to humidity is formed on the silicon nitride film 40 so as to cover the electrodes 31, 32, and the gaps formed therebetween. In this embodiment, the moisture-sensitive film 50 is disposed between the electrodes 31, 32 so that a lower surface thereof is located lower than surfaces 31s, 32s of the electrodes 31, 32 as shown in FIG. 2, whereby the moisture-sensitive film 50 is interposed between the electrodes 31, 32.

A hygroscopic macro molecule organic material can be employed as the moisture-sensitive film 50. Specifically, polyimide or butyric acetylcellulose or the like can be employed. In this embodiment, the film 50 is composed of polyimide. When water molecular is absorbed in the film 50, the permittivity of the film 50 changes according to amount of absorbed water molecules since water molecules have high permittivity to thereby cause change in capacitance between the detection electrodes 31, 32.

An area where the moisture-sensitive film 50 is located on the semiconductor substrate 10 constitutes a humidity-sensing portion 100. Namely, ambient humidity is detected by the humidity-sensing portion 100 based on the capacitance formed between the detection electrodes 31, 32 that changes according to a change in humidity around the sensor S1.

A circuit element portion 200 is formed in an area excluding the area where the humidity-sensing portion 100 is located (a periphery of the humidity-sensing portion 100, which is indicated by hatching in FIG. 1). The circuit element portion 200 produces a signal indicative of the capacitance formed between the detection electrodes 31, 32.

As shown in FIG. 2, the circuit element portion 200 includes, for example, a C-MOS transistor 210 in this embodiment. The C-MOS transistor 210 has a P-channel MOS transistor and an N-channel MOS transistor, each of which has a gate electrode 211 composed of poly-Si, Al wirings 212 that are electrically conducted to a source and a drain. Moreover, the C-MOS transistor 210 has a reference capacitance portion 213, which in turn has a wiring electrode 213a composed of poly-Si.

Incidentally, the circuit element portion 200 may have other circuit elements such as bi-polar transistors or the like.

In this embodiment, although not shown in FIG. 2, an oscillating circuit 350 (FIG. 4) or the like is formed in a manner that will be described later.

Next, a manufacturing process will be explained with reference to FIGS. 3A–3C.

Figure 3A:
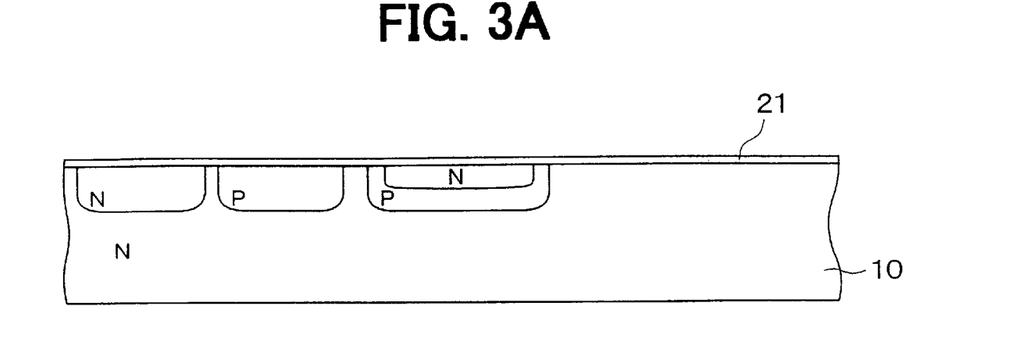
FIGS. 3A to 3C are schematic cross sectional views taken along line III—III in FIG. 1, showing a manufacturing method of the capacitance type humidity sensor of the present invention.

As shown in FIG. 3A, diffusion regions and a thermal oxidation film 21 are formed on the silicon substrate 10 by ion implantation, thermal diffusion and thermal oxidizing. Next, as shown in FIG. 3B, source and drain diffusion regions and poly-Si electrodes 211, 213a are formed on the silicon substrate 10 by ion implantation, thermal diffusion, CVD (Chemical Vapor Deposition) and patterning, whereby the circuit element portion 200 is formed on the silicon substrate 10.

Subsequently, a silicon oxide film is formed on the thermal oxidation film by CVD to form a silicon oxide film 20 as the first insulation film with the thermal oxidation film 21.

Figure 3B:
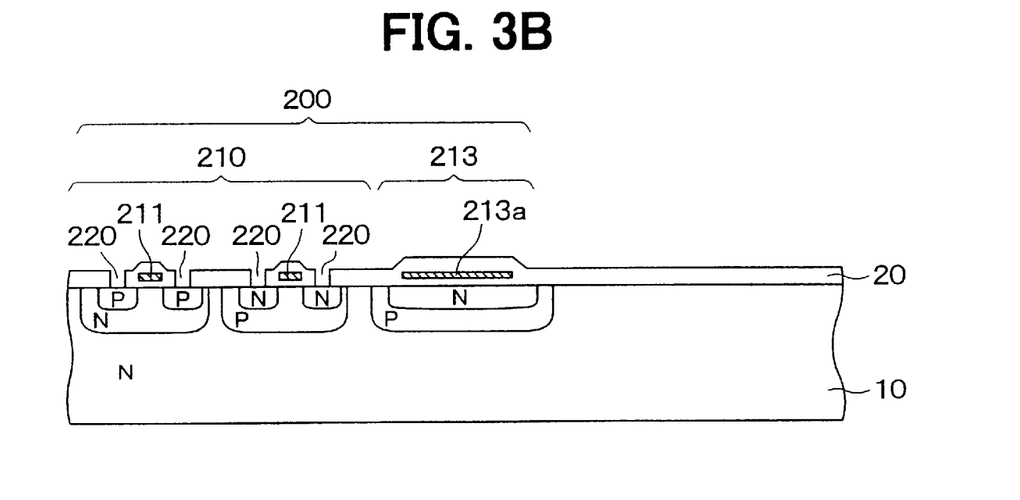

Further, as shown in FIG. 3B, contact holes 220 for making electrical contact between the circuit element portion 200 and wiring electrodes thereof are formed in the silicon oxide film 20 by etching using a conventional photolithography method.

Next, as shown in FIG. 3B, the wiring electrodes of the circuit element portion 200 and the detection electrodes 31, 32 for detecting changes in humidity are formed by a sputtering or deposition method using Al or the like. The silicon nitride film 40 (second insulation film) is formed on the electrodes by plasma CVD or the like as shown in FIG. 3C.

Next, pad portions (not shown) for connecting the circuit element portion 200 to an external device are opened in the silicon nitride film 40.

Finally, the moisture-sensitive film 50 is formed on the silicon nitride film 40 by a method in which polyimide is formed on the nitride film 40 by spin coating, and is hardened and then patterned by photo-etching, or by a method in which polyimide is formed on the nitride film 40 by printing method and is hardened. Thus, the capacitance type humid sensor S1 is completed in a typical semiconductor producing line.

Figure 4:
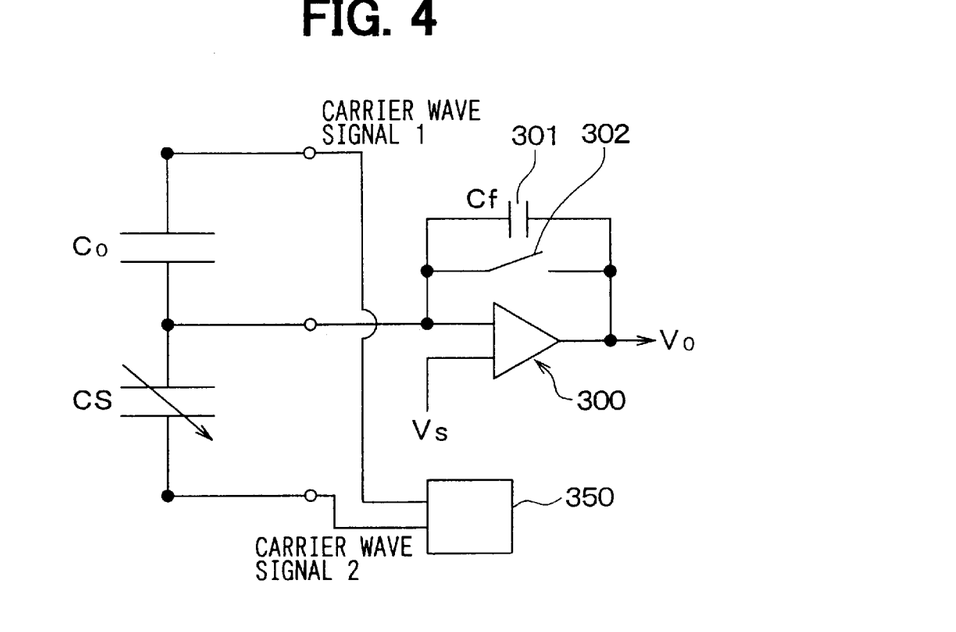
FIG. 4 is a schematic circuit diagram of the capacitance type humidity sensor of the present invention.

Next, operation of the sensor S1 will be explained with reference to FIG. 4. In the sensor S1, the respective detection electrodes 31, 32 are electrically connected to the circuit element portion 200 to form a switched capacitor circuit as shown in FIG. 4.

CS denotes a variable capacitance that is formed by the opposing detection electrodes 31, 32, and that changes according to humidity conditions. Co is a reference capacitance which is formed between the wiring electrode 213a and the silicon substrate 10 disposed below at the reference capacitance portion 213.

A differential amplifier circuit 300 consists of the C-MOS transistor 210 and the like to detect intermediate potential between the reference capacitance Co and the variable capacitance CS. The differential amplifier circuit 300 has a switch 302 and a capacitor 301 having capacitance Cf. A reference potential Vs is inputted to the amplifier circuit 300.

Figure 5:
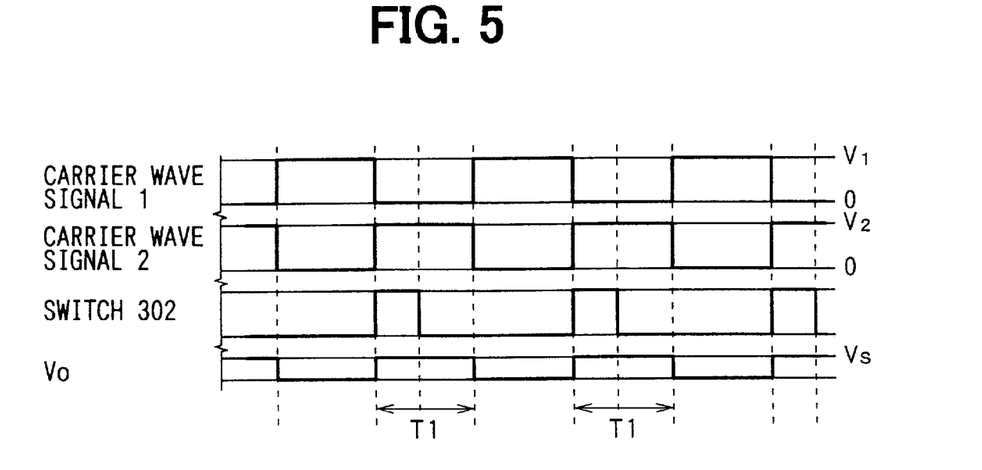
FIG. 5 is a timing chart for the circuit diagram in FIG. 4.

Moreover, the circuit element portion 200 has an oscillating circuit 350 for sending two carrier wave signals in opposite phase from each other respectively to one electrode of the reference capacitance Co (for example, the silicon substrate 10) and one of the detection electrodes 31, 32 (one electrode of the variable capacitance CS). A sample chart of waveforms associated with the detection circuit is shown in FIG. 5.

Specifically, a carrier wave signal 1 (an amplitude: 0-V1) is impressed on the one electrode of the reference capacitance Co, and a carrier wave signal 2 (an amplitude: 0-V2) 180° out of phase with the carrier wave 1 is impressed on the one electrode of the variable capacitance CS. The switch 302 is turned on and off according to timing shown in FIG. 5.

The intermediate potential formed between the variable capacitance CS and the reference capacitance Co is outputted as an output voltage Vo through the differential amplifier circuit 300 at detection period T1. At this time, the variable capacitance CS changes in accordance with sensed humidity while the reference capacitance Co does not change, to thereby cause change in the intermediate potential. Namely, the humidity can be detected using the output voltage Vo.

In this embodiment, since the silicon nitride film 40 is interposed between the detection electrodes 31, 32 and the moisture-sensitive film 50, the detection electrodes 31, 32 are protected against water passing through the moisture-sensitive film 50, whereby moisture resistance of the detection electrodes 31, 32 can be secured.

Therefore, it is not necessary to use a particular metal having excellent moisture resistance such as a precious metal for the detection electrodes 31, 32, and therefore a material (for example, aluminum) that does not become a contaminant in the normal semiconductor producing line can be employed for the detection electrodes 31, 32.

Moreover, a leak current can be prevented from flowing between the detection electrodes 31, 32 by interposing the silicon nitride film 40 therebetween. Incidentally, detection electrodes of the resistance detection type sensor mainly disclosed in JP-A-7-20080 cannot be covered with an insulation film because current must flow between the electrodes.

As described above, a highly reliable capacitance type humidity sensor can be provided that can be composed of a material that is capable of being used in a typical semiconductor producing line.

Furthermore, a typical semiconductor producing technique can be employed prior to forming the moisture-sensitive film 50, so that high integration and miniaturization of the sensor including the detection electrodes 31, 32 can be achieved. Especially, polyimide is suitable for the semiconductor process since it is usually used for a protection film for a semiconductor device.

Moreover, in this embodiment, the circuit element portion 200 and the detection electrodes 31, 32 are integrated in the same silicon substrate 10, so that stray capacitance formed therebetween can be prevented from increasing. As a result, the S/N ratio of the device can be improved so that the detection electrodes 31, 32 can be miniaturized to thereby miniaturize the size of the capacitance type humidity sensor.

Preferably, a material capable of coating and being hardened at a temperature of 400° C. or less is employed for the moisture-sensitive film 50 because treatment at a temperature of 400° C. or less may not influence the properties of the semiconductor element. Incidentally, polyimide can be hardened at a temperature of 350° C.

Preferably, the detection electrodes 31, 32 are composed of an identical material as the material used to form the wiring electrodes 212 formed in the circuit element portion 200, so that the electrodes 31, 32 can be formed in the same process as that for forming the wiring electrodes of the circuit element portion 200.

Figure 3C:
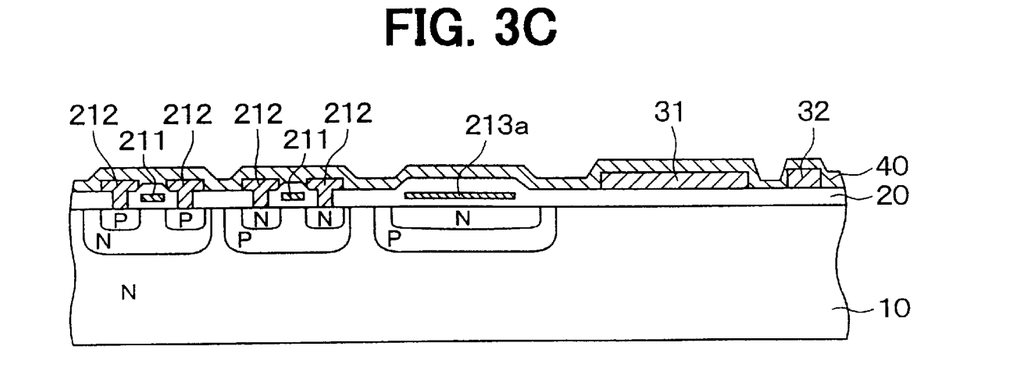

For example, in the step shown in FIG. 3C, the detection electrodes 31, 32 and the wiring electrodes of the circuit element portion 200 both can be formed by a sputtering or deposition method using Al, so that the number of process steps can be decreased. Moreover, a mask for forming the detection electrodes 31, 32 is not required.

Further, although other material can be employed as the second insulation film to cover the detection electrodes 31, 32, silicon nitride film is suitable since it has relatively high permittivity among insulation films, thereby decreasing loss of capacitance between the detection electrodes 31, 32, so that its detection sensitivity can be higher.

Preferably, a material that has a lower permittivity in comparison with silicon nitride film is employed as the first insulation film, such as silicon oxide film, although silicon nitride film can be employed as the first insulation film. Such a material can decrease parasitic capacitance between the detection electrodes 31, 32 and the silicon substrate 10, so that detection sensitivity can be higher.

Moreover, as shown in FIG. 2, since the moisture-sensitive film 50 is disposed lower than the surfaces 31s, 32s of the detection electrodes 31, 32, the moisture-sensitive film 50 is disposed in the gap formed between the detection electrodes 31, 32 to thereby increasing detection sensitivity.

Moreover, the circuit element portion 200 includes the switched capacitor circuit that converts capacitance to voltage. The switched capacitor circuit can sensitively detect minute changes in capacitance so that the detection electrodes can be miniaturized.

Incidentally, it is not necessarily to integrate the humidity-sensing portion 100 with the circuit element portion 200. In this case, a chip or board containing the circuit element portion 200 can be electrically connected to the substrate having the humidity-sensing portion 100 by lead wirings or bonding wirings.

(Second Embodiment)

A humidity sensor of the second embodiment will be described with reference to FIGS. 6 to 10. These sensors are similar to the humid sensor S1 described above, and shown in FIGS. 1 to 5. Features that are different from the first embodiment will be explained hereinafter.

Figure 6:
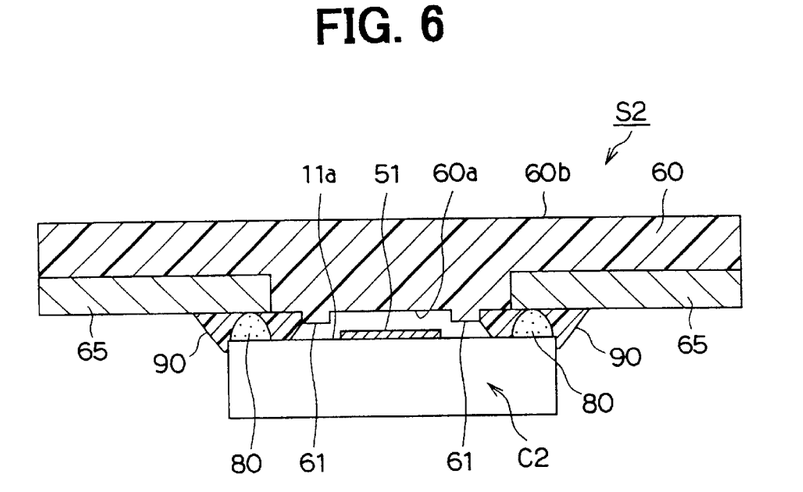
FIG. 6 is a schematic cross sectional view of a capacitance type humidity sensor of a second embodiment of the present invention.

As shown in FIG. 6, a humid sensor S2 includes two primary components. A sensor chip C2 is fixed to a supporting substrate 60 through connecting electrodes 80, with a gap interposed therebetween so that a moisture-sensitive film 51 is exposed to the gap. In other words, a principal surface 60a of the supporting substrate 60 faces a principal surface 11a of the sensor chip C2.

The supporting substrate 60 has terminal electrodes 65 at the principal surface 60a that are electrically connected to an external circuit or the like, to receive power, to send electrical signals or the like. The supporting substrate 60 is composed of, for example, resin, ceramic or the like. The terminal electrodes 65 are composed of conductive material such as, for example, Cu(copper), 42-alloy or the like.

In this embodiment, the terminal electrodes 65 are integrated in the supporting substrate 60 by insert molding with resin. The supporting substrate 60 may be mounted on a circuit substrate (not shown) at a back surface 60b thereof, so that the sensor chip C2 is electrically connected to the circuit substrate through the terminal electrode 65. Incidentally, the supporting substrate 60 and terminal electrodes 65 are only partially shown in FIG. 6.

Figure 7:
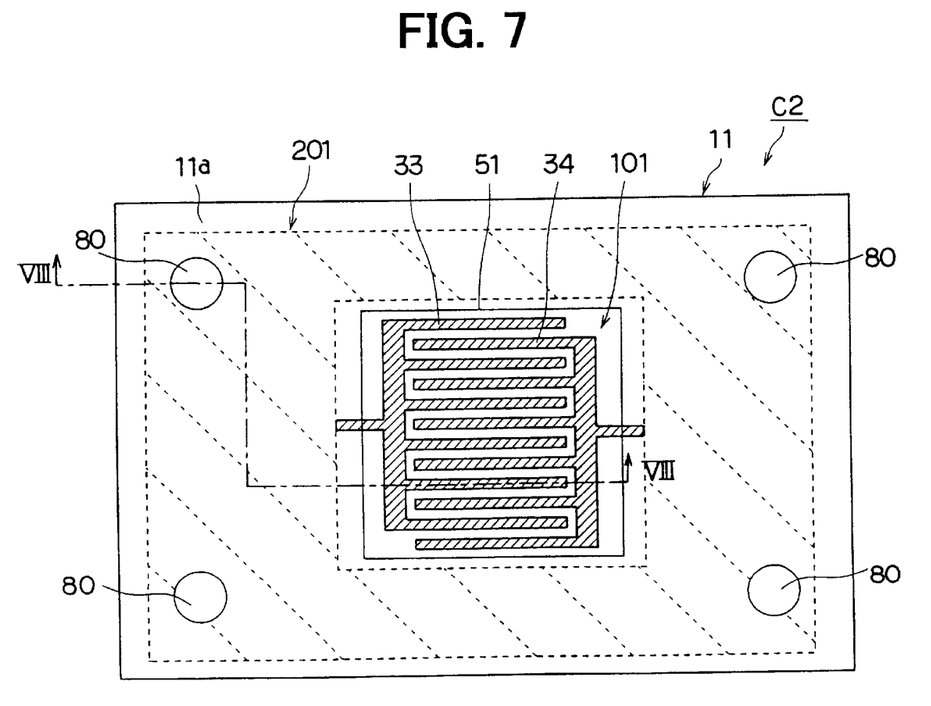
FIG. 7 is a schematic plan view of a sensor chip of the second embodiment.
Figure 8:
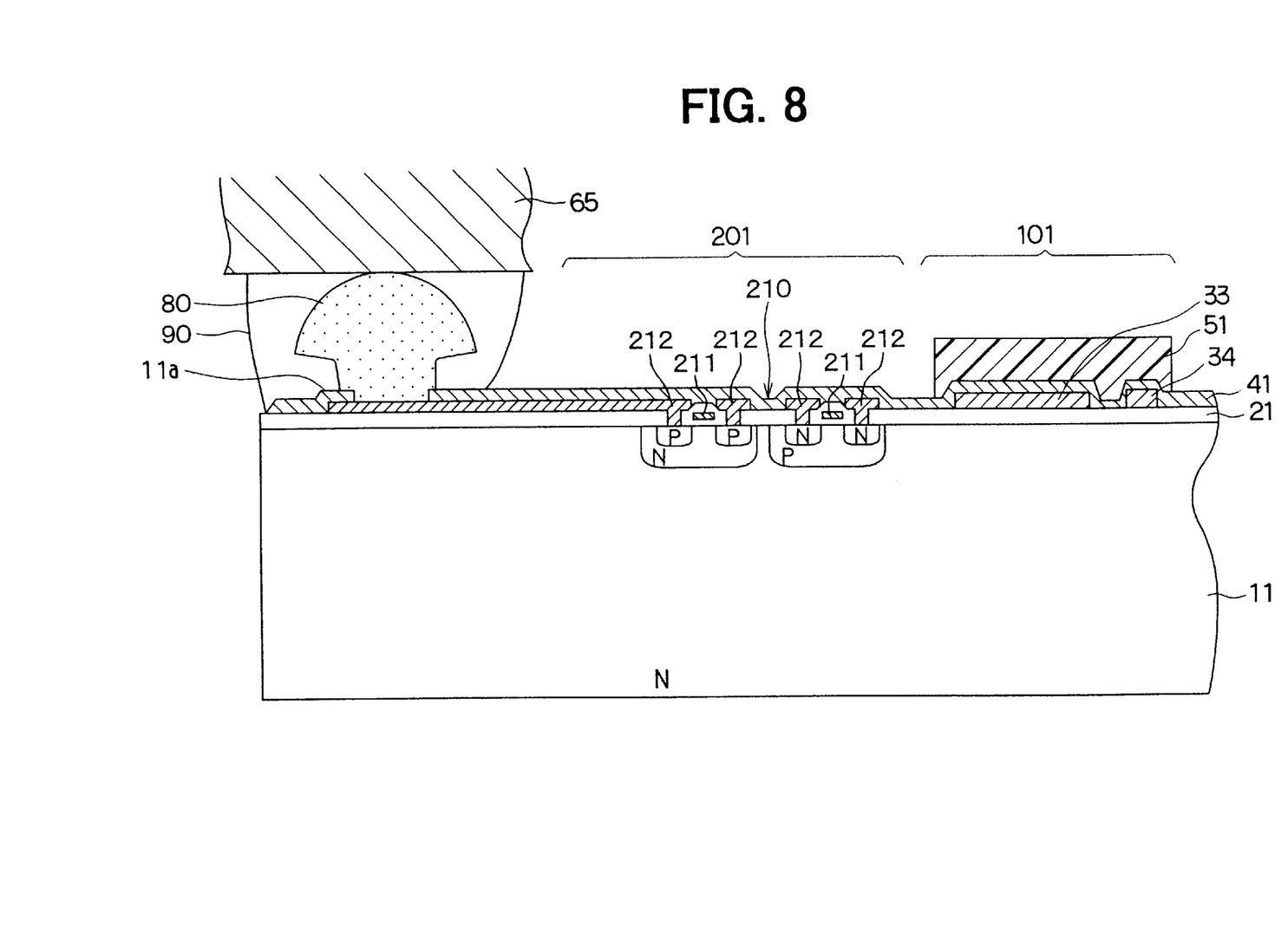
FIG. 8 is a part of a cross sectional view taken along line VII—VII in FIG. 7.

As shown in FIGS. 6, 7 and 8, the sensor chip C2 has a structure similar to that of the sensor S1 shown in FIGS. 1 and 2. Namely, the chip C2 has a humidity-sensing portion 101 and a circuit element portion 201 so as to surround the humidity-sensing portion 101.

In the humidity-sensing portion 101, detection electrodes 33, 34 for detecting atmosphere humidity around the chip C2 are formed and covered by silicon nitride film 41. Moreover, a moisture-sensitive film 51 is disposed on the humidity-sensing portion 101 as shown in FIG. 8.

In the circuit element portion 201, a C-MOS transistor 210 is shown in FIG. 8. The C-MOS transistor 210 has a P-channel MOS transistor and a N-channel MOS transistor each of which has a gate electrode 211 composed of poly-Si, Al wirings 212 that are electrically connected to a source and a drain. Although not shown in FIGS. 6 to 8, the circuit element portion has other circuit elements for constituting a switched capacitor circuit or the like to process signals from the humidity-sensing portion 101, and output the modified signals to the external circuit through the terminal electrode 65, as described in first embodiment. Namely, a signal indicating change in capacitance at the humidity-sensing portion 101 is converted into a voltage signal at the circuit element portion 201. Therefore, humidity around the sensor S2 can be detected according to the voltage signal.

Incidentally, the circuit element portion 201 is represented by hatching in FIG. 7. Also, the circuit element portion 201 is covered by the silicon nitride film 41. The circuit element portion 201 may not be covered with the moisture-sensitive film 51.

Moreover, at a side of the principal surface 11a, bump electrodes 80 are provided at a peripheral portion of the sensor chip C2 for connecting the wirings in the circuit element portion 201 to the terminal electrodes 65. The bump electrodes 80 are composed of solder, Au, Cu or the like. In this embodiment, solder is employed as the bump electrodes 80.

The exemplary bump electrode 80 shown in FIG. 8 is connected to the wiring 212 in the circuit element portion 201 through an opening formed in the silicon nitride film 80. Namely, the detection electrodes 33, 34 are connected to the bump electrodes 80 through the wiring 212.

As shown in FIG. 6, the bump electrodes 80 are connected to the terminal electrodes 65, each of which is covered with coating material 90. The coating material 90 is composed of resin material such as epoxy resin, silicone gel, or insulative material. In this embodiment, the coating material 90 is composed of resin material.

Moreover, as shown in FIG. 6, at a side of the principal surface of the supporting substrate 60, protrusions 61 are provided on the supporting substrate 60 so as to protrude toward the sensor chip C2. Each of the protrusions 61 is provided between a portion of the supporting substrate 60 that faces the bump electrode 80 and a portion of the supporting substrate 60 that faces the moisture-sensitive film 51, as a partition to prevent the coating material 90 from flowing toward a region of the supporting substrate that faces the moisture-sensitive material 51. The protrusions 61 may be formed as a single protrusion so as to surround the region of the supporting substrate that faces the moisture-sensitive material 51.

The sensor chip C2 is basically produced by following the manufacturing steps of sensor chip S1 shown in FIGS. 3A to 3C. Portions of the silicon nitride film are then removed to expose the part of wirings 212 by etching using photolithography to form contact holes through which the bump electrodes 80 are contacted to the wirings 212. Next, the bump electrodes 80 are formed using plating, depositing or the like so as to be contacted to the wirings 212 through the contact holes. Then, similarly to the first embodiment, the moisture-sensitive film 51 is formed on the humidity-sensing portion 101. Actually, the sensor chip C2 is diced from a semiconductor wafer.

Next, the diced sensor chip C2 is mounted on the principal surface 60a of the supporting substrate 60 so that the bump electrodes 80 are contacted to the terminal electrodes 65. Then, the bump electrodes 80 are bonded to the terminal electrodes 65 by reflow-soldering by heating the bump electrodes 80.

After that, resin material is deposited around the bump electrodes 80 using a dispenser or the like and hardened to form the coating material 90. Finally, the sensor S2 shown in FIG. 6 is completed.

As described above, according to this embodiment, at the side of the principal surface 11a of the sensor chip C2, the detection electrodes 33, 34 and wiring-electrodes in the circuit element portion 201 including the wirings 212 are protected by the silicon nitride film 41 except the portions where the bump electrodes 80 are contacted. Moreover, the bump electrodes 80 and bonding portions, where the bump electrodes 80 are contacted to the wirings 212, are covered by the coating material 90.

Therefore, the sensing electrodes 33, 34 and the wirings 212 formed on the principal surface 11a of the sensor chip C2 are prevented from exposure to the humidity being measured. Therefore, a material capable of being employed in a normal semiconductor process, that has a non-corrosive resistance such as aluminum or a material whose main component is aluminum-alloy, can be employed as a material for the electrodes 33, 34 and wirings 212.

In this connection, a sensor having sensing electrodes, which are made of a specific corrosive resistant material (a fusible conductive high polymer compound) formed on a substrate, is disclosed in JP-A-5-45320. That material, however, is not suitable for a normal semiconductor mass production process because the material can become a contaminant for semiconductor elements such as a C-MOS transistor. Therefore, the cost of producing that kind of sensor is increased.

To the contrary, according to the first and second embodiments, the sensor chip having the circuit element portion for signal processing as well as the humidity-sensing portion can be produced by a normal semiconductor process. Therefore, this kind of sensor can be miniaturized, highly-integrated and mass-produced. As a result, a humidity detection sensor that is inexpensive and highly reliable can be obtained.

Moreover, according to the second embodiment, since the sensor chip C2 is integrated on the supporting substrate 60 having the terminal electrodes 65, the mounting area for the sensor chip can be reduced, resulting in miniaturization of the sensor.

Moreover, the protrusions 61 prevent the coating material 90 from flowing into an area facing the moisture-sensitive film 51 when the coating material 90 is deposited.

Other features of this embodiment are similar to that of the first embodiment.

Figure 9:
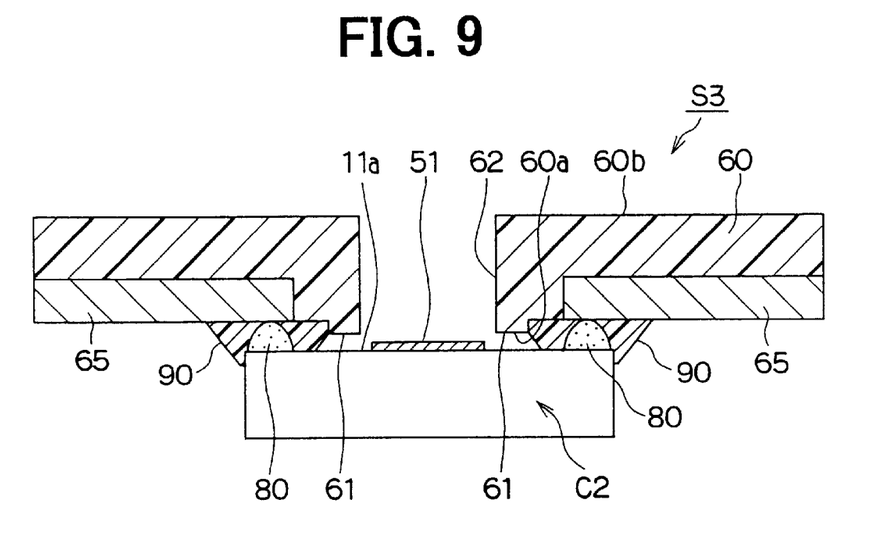
FIG. 9 is a schematic cross sectional view of a modified capacitance type humidity sensor of the second embodiment.
Figure 10:
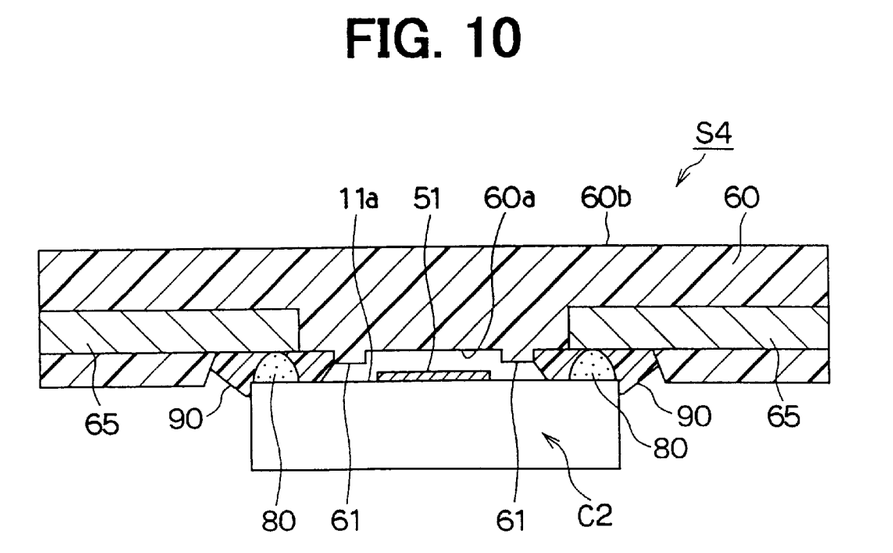
FIG. 10 is a schematic cross sectional view of a modified capacitance type humidity sensor of the second embodiment.

Next, modifications of the second embodiment are shown in FIGS. 9 and 10. These figures show cross sectional views of modified sensors S3 and S4.

As shown in FIG. 9, an opening portion 62 is formed in and penetrates the supporting substrate 60, which faces the moisture-sensitive film 51. This opening portion 62 provides additional exposure to the humidity to be detected by the sensor chip C2 by being wide-open around the moisture-sensitive film 51. Therefore, the response of the sensor chip C2 can be improved.

As shown in FIG. 10, the terminal electrodes 65 are buried in the supporting substrate when the insert molding is conducted to prevent exposure to the humidity to be detected. Therefore, the terminal electrodes 65 are also protected from moisture.

Although the above-described embodiments disclose integrated-type sensors each of which has a circuit element portion as well as a humidity-sensing portion, the circuit element portion may be separated from the sensor chip. Namely, the sensor chip may be produced to have only the humidity-sensing portion as a so-called discrete-type sensor chip. This sensor chip can be connected to an external signal-processing circuit through lead electrodes or bonding wirings.

In this case, the detection electrodes 33, 34 are directly connected to the bump electrodes 80, so that parts of the detection electrodes 80 are not covered by the silicon nitride film 41 but rather by the coating material 90.

Therefore, similarly to the second embodiment, the detection electrodes or bump electrodes are prevented from being exposed to the circumstance to be detected. Consequently, the discrete-type sensor also can be produced in the normal semiconductor process so as to be inexpensive and reliable.

Incidentally, other semiconductor substrates can be employed instead of the silicon substrate.

While the present invention has been shown and described with reference to the foregoing preferred embodiment, it will be apparent to those skilled in the art that changes in form and detail may be therein without departing from the scope of the invention as defined in the appended claims.

What is claimed is:

1. A capacitance type humidity sensor comprising:
   a semiconductor substrate;
   a first insulation film formed on the semiconductor substrate;
   two electrodes formed on the first insulation film so as to oppose each other with a gap interposed therebetween;
   a second insulation film formed on the two electrodes so as to cover the two electrodes; and
   a moisture-sensitive film that directly contacts the second insulation film so as to cover the two electrodes, the moisture-sensitive film having a capacitance which changes according to ambient humidity,
   wherein the moisture-sensitive film is provided such that a capacitance formed between the two electrodes changes according to the ambient humidity.

2. A capacitance type humidity sensor according to claim 1, further comprising:
   a circuit portion formed on the semiconductor substrate to process a signal that contains a change in the capacitance formed between the two electrodes.

3. A capacitance type humidity sensor according to claim 2, wherein the two electrodes are composed of a material identical with that forming wiring material in the circuit portion.

4. A capacitance type humidity sensor according to claim 2, wherein the circuit portion has a switched capacitor circuit which converts the change in the capacitance formed between the two electrodes.

5. A capacitance type humidity sensor according to claim 1, wherein the second insulation film includes silicon nitride.

6. A capacitance type humidity sensor according to claim 5, wherein the first insulation film is composed of a material that has lower permittivity than that of silicon nitride.

7. A capacitance type humidity sensor according to claim 1, wherein the moisture-sensitive film comprises a hygroscopic macro-molecule organic material.

8. A capacitance type humidity sensor comprising:
   a semiconductor substrate;
   a first insulation film formed on the semiconductor substrate;
   two electrodes formed on the first insulation film so as to oppose each other with a gap interposed therebetween;
   a second insulation film formed on the two electrodes so as to cover the two electrodes; and
   a moisture-sensitive film formed on the second insulation film so as to cover the two electrodes, the moisture-sensitive film having a capacitance which changes according to ambient humidity,
   wherein a capacitance formed between the two electrodes changes according to the ambient humidity, and
   the two electrodes each have a plurality of tooth portions to form a comb-shaped pattern, the plurality of tooth portions of one of the two electrodes being interleaved with the plurality of tooth portions of a second of the two electrodes.

9. A capacitance type humidity sensor according to claim 1, wherein the two electrodes are formed from a material selected from a group consisting of Al, Al—Si, Ti, Au, Cu, poly-Si.

10. A capacitance type humidity sensor according to claim 1, wherein the two electrodes are a combination made by two or more materials selected from a group consisting of Al, Al—Si, Ti, Au, Cu, poly-Si.

11. A capacitance type humidity sensor according to claim 1, wherein the moisture-sensitive film is disposed lower than top surfaces of the two electrodes.

12. A capacitance type humidity sensor comprising:
a semiconductor substrate;
a first insulation film formed on the semiconductor substrate;
two electrodes formed on the first insulation film so as to oppose each other with a gap interposed therebetween;
a second insulation film formed on the two electrodes so as to cover the two electrodes; and
a moisture-sensitive film formed on the second insulation film so as to cover the two electrodes, the moisture-sensitive film having a capacitance which changes according to ambient humidity,
wherein a capacitance formed between the two electrodes changes according to the ambient humidity, and
a supporting substrate having a wiring electrode portion to be externally electrically connected,
wherein the semiconductor substrate is mounted on the supporting substrate, and wherein a change in capacitance formed between the two electrodes is externally outputted through the wiring electrode portion.

13. A capacitance type humidity sensor according to claim 12, further including:
a connecting electrode portion is formed on a principal surface of the semiconductor substrate, where the two electrodes are formed, wherein:
the semiconductor substrate is mounted on the supporting substrate so that the connecting electrode portion is connected to the wiring electrode portion of the supporting substrate, and so that the moisture-sensitive film opposes a principal surface of the supporting substrate with a gap interposed therebetween.

14. A capacitance type humidity sensor according to claim 13, further including:
a wiring portion formed on the first insulation film, disposed between the two electrodes and the connecting electrode portion, and connected to the connecting electrode portion so as to electrically connect the two electrodes and the connecting electrode portion, wherein the wiring portion is covered by the second insulation film; and
a coating material covering the connecting electrode portion.

15. A capacitance type humidity sensor according to claim 14, further including:
a circuit element portion disposed between the wiring portion and the two electrodes to process signals obtained from the two electrodes.

16. A capacitance type humidity sensor according to claim 14, wherein the wiring portion and the two electrodes are composed of a same material.

17. A capacitance type humidity sensor according to claim 14, further comprising:
a protrusion portion formed on the principal surface of the supporting substrate so as to be disposed between a first area of the supporting substrate opposing the moisture-sensitive film and a second area of the supporting substrate being connected to the connecting electrode portion.

18. A capacitance type humidity sensor according to claim 17, wherein said protrusion portion surrounds the first area.

19. A capacitance type humidity sensor comprising:
a supporting substrate having a wiring electrode portion to be externally electrically connected;
a sensing base mounted on the supporting substrate so that a principal surface thereof opposes a principal surface of the supporting substrate;
a moisture-sensitive film formed on the principal surface of the sensing base with a space apart from the principal surface of the supporting substrate;
a detection electrode portion to detect a change in capacitance of the moisture-sensitive film;
a connecting electrode portion formed on the principal surface of the sensing base so as to be electrically connected to the wiring electrode portion and the detection electrode portion;
a protection film covering the detection electrode portion except a bonding portion thereof which is connected to the connecting electrode portion; and
a coating material covering the connecting electrode portion.

20. A manufacturing method of a capacitance type humidity sensor, comprising:
forming a first insulation film on a semiconductor substrate after a circuit portion is formed on a semiconductor substrate;
forming wiring electrodes of the circuit portion and two electrodes for detecting a change in capacitance on the first insulation film;
forming a second insulation film on the two electrodes to cover the two electrodes; and
forming a moisture-sensitive film on the second insulation film, the moisture-sensitive film directly contacting the second insulation film so as to cover the two electrodes, wherein the moisture-sensitive film has a capacitance which changes according to ambient humidity.

21. A manufacturing method of capacitance type humidity sensor according to claim 20, wherein the two electrodes and the wiring electrode of the circuit portion are simultaneously formed.

22. A capacitance type humidity sensor according to claim 1, wherein the second insulation film is interposed between the moisture-sensitive film and the two electrodes.

23. A capacitance type humidity sensor according to claim 1, wherein the second insulation film is disposed in the gap between the two electrodes to separate the two electrodes from each other.

24. A capacitance type humidity sensor according to claim 1, wherein:
the two electrodes have first surfaces contacting the first insulation film, second surfaces opposite to the first surfaces, and side end surfaces between the first surfaces and the second surfaces; and
the second insulation film covers at least the second surfaces as well as the side end surfaces of the two electrodes between the two electrodes and the moisture-sensitive film.

* * * * *